United States Patent
Wetzler et al.

(10) Patent No.: US 10,280,194 B2
(45) Date of Patent: May 7, 2019

(54) SHORT CHAIN PEGYLATION OF AMINO ACID MONOMERS GLUTAMINE, LYSINE AND PEPTIDES FORMED THEREBY

(71) Applicant: Clemson University, Clemson, SC (US)

(72) Inventors: Modi Wetzler, Clemson, SC (US); Paris Lamont Hamilton, Central, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 15/317,208

(22) PCT Filed: Jun. 8, 2015

(86) PCT No.: PCT/US2015/034651
§ 371 (c)(1),
(2) Date: Dec. 8, 2016

(87) PCT Pub. No.: WO2015/191433
PCT Pub. Date: Dec. 17, 2015

(65) Prior Publication Data
US 2017/0137460 A1    May 18, 2017

Related U.S. Application Data

(60) Provisional application No. 62/009,433, filed on Jun. 9, 2014.

(51) Int. Cl.
*C07C 229/26* (2006.01)
*C07K 2/00* (2006.01)
(Continued)

(52) U.S. Cl.
CPC .......... *C07K 1/006* (2013.01); *C07C 229/26* (2013.01); *C07C 237/12* (2013.01);
(Continued)

(58) Field of Classification Search
CPC .... C07C 229/26; C07K 1/006; C07K 1/1077; C07K 1/113; C07K 2/00
See application file for complete search history.

(56) References Cited

U.S. PATENT DOCUMENTS

| 4,324,743 A * | 4/1982 | Feuer | A61K 8/44 562/106 |
| 4,851,385 A * | 7/1989 | Roeske | C07K 7/23 514/10.1 |
| 2010/0203645 A1* | 8/2010 | Dratz | C07F 5/022 436/86 |

FOREIGN PATENT DOCUMENTS

WO    WO 99/03399 A1    1/1999

OTHER PUBLICATIONS

Vita et al. Synthesis of N6,N6-Bis(2-chloroethyl)-DL-lysine. Journal of Medicinal Chemistry. Jul. 1964, vol. 7, No. 4, pp. 468-471.*
(Continued)

*Primary Examiner* — Jeffrey E. Russel
(74) *Attorney, Agent, or Firm* — Joseph T. Guy; Patent Filing Specialist, Inc.

(57) ABSTRACT

Novel synthesized amino acids of glutamine and lysine that are directly PEGylated with small, monodisperse PEGs, and a novel process for creating novel amino acid monomers using PEGylation. These amino acids are readily incorporated into peptides for a range of different applications.

64 Claims, 4 Drawing Sheets

(51) Int. Cl.
*C07K 1/00* (2006.01)
*C07K 1/06* (2006.01)
*C07C 271/22* (2006.01)
*C07C 237/12* (2006.01)

(52) U.S. Cl.
CPC ............ *C07C 271/22* (2013.01); *C07K 1/066* (2013.01); *C07K 2/00* (2013.01)

(56) References Cited

OTHER PUBLICATIONS

De Blas et al. Solid phase synthesis of glutamic acid derivatives via nucleophilic ring opening of N-Boc pyroglutamate with heteronucleophiles. Tetrahedron Letters. 2000, vol. 41, pp. 4567-4571. (Year: 2000).*

Kimura et al. Influence of Alkylamides of Glutamic Acid and Related Compounds on the Central Nervous System . . . Chemical and Pharmaceutical Bulletin. 1971, vol. 19, No. 7, pp. 1301-1307. (Year: 1971).*

Toho et al. Synthesis of N1- and N8-(gamma-L-Glutamyl)spermidines and (gamma-L-Glutamyl)putrescine. Letters in Organic Chemistry. 2011, vol. 8, No. 1, pp. 1-4. (Year: 2011).*

Vita et al. "Synthesis of N6,N6-Bis(2-chloroethyl)-DL-lysine", J. Med. Chem., vol. 7, 1964, pp. 468-471.

Harris, J. Milton et al. "Effect of Pegylation on Pharmaceuticals". Nature Reviews, Drug Disco, Nature Publishing Group, vol. 2, No. 3, Mar. 1, 2003.

Harris, J. Milton et al. "Pegylation—A Novel Process for Modifying Pharmacokinetics" Clin Pharmacokinet 2001; pp. 539-551.

Hendler, Richard W. "On the Agreement of Amino Acid Replacement Data with Code Designations for the Amino Acids" Laboratory of Cellular Physiology and Metabolism, vol. 48 (1962).

European Patent Office; Supplementary European Search Report; EP 15 80 6442; Jan. 9, 2018.

* cited by examiner

SHORT CHAIN PEGYLATION OF AMINO ACID MONOMERS GLUTAMINE, LYSINE AND PEPTIDES FORMED THEREBY

CROSS-REFERENCE TO RELATED APPLICATIONS

This application claims priority to pending U.S. Provisional Patent Appl. No. 62/009,433 filed Jun. 9, 2014, which is incorporated herein by reference.

BACKGROUND

The invention relates to novel PEGylated compounds and a process for formation of PEGylated compounds. More specifically, the present invention is related to novel PEGylated compounds, primarily PEGylated amino acid monomers and their use in the formation of advanced peptides. The invention provides synthesized amino acids of glutamine and lysine that are directly PEGylated with multiple small, monodisperse PEGs. These amino acids are readily incorporated into peptides for a range of different applications.

PEGylation is a process of attaching strands of polymeric polyethylene glycol (PEG) to molecules, most typically peptides, proteins, and antibody fragments, that can help to meet the challenges of improving the safety and efficiency of many therapeutics. PEGylation produces alterations in the physiochemical properties including changes in conformation, electrostatic binding, hydrophobicity, and the like. These physical and chemical changes increase systemic retention of the therapeutic agent. PEGylation can also influence the binding affinity of the therapeutic moiety to the cell receptors and can alter the absorption and distribution patterns.

By increasing the molecular weight of a molecule, PEGylation can impart several significant pharmacological advantages over the unmodified form. Advantages include improved drug solubility, reduced dosage frequency without diminished efficacy, potentially a reduced toxicity, an extended circulating life, increased drug stability and enhanced protection from proteolytic degradation.

PEG is a particularly attractive polymer for conjugation. The specific characteristics of PEG moieties relevant to pharmaceutical applications are water solubility, high mobility in solution, lack of toxicity and low immunogenicity, ready clearance from the body and altered distribution in the body.

The overall PEGylation processes used to date for protein conjugation can be broadly classified into two types, namely a solution phase batch process and an on-column fed-batch process. The simple and commonly adopted batch process involves the mixing of reagents together in a suitable buffer solution, preferably at a temperature between 4° C. and 6° C., followed by the separation and purification of the desired product using a suitable technique based on its physico-chemical properties, including size exclusion chromatography (SEC), ion exchange chromatography (IEX), hydrophobic interaction chromatography (HIC) and membranes or aqueous two phase systems.

The techniques used to form first generation PEG derivatives are generally reacting the PEG polymer with a group that is reactive with hydroxyl groups, typically anhydrides, acid chlorides, chloroformates and carbonates. In the second generation PEGylation chemistry more efficient functional groups are made available for conjugation such as aldehyde, esters, amides etc.

As applications of PEGylation have become more and more advanced and sophisticated, there has been an increase in the need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and N-hydroxysuccinimide (NHS) esters.

Third generation PEGylation agents, where the shape of the polymer has been branched, Y shaped or comb shaped are available which show reduced viscosity and lack of organ accumulation.

Dozens of peptide drugs are on the market but the difficulty in forming PEGylated peptides is evident by the lack of any appreciable PEGylated peptides and currently there are no PEGylated peptides of commercial significance. Like with larger proteins, PEGylation of peptides can increase solubility and reduce cleavage of the peptides by proteases in the blood, both of which are severe problems for peptide drugs. For example, Victoza®, (liraglutide, Novo Nordisk) the first non-insulin peptide blockbuster drug, is a GLP-1 mimic; the half-life of GLP-1 in blood is 90 seconds.

Most PEGylation strategies are designed for large proteins wherein long PEGs are used to impart the desired properties. The long PEGs, however, are too big for peptides. In practice, peptide modification sites are limited primarily to lysines and the N-terminus, although all the same reactive side chains of proteins (cysteines, aspartic acids, glutamic acids, serines, threonines, histidines) could in theory be modified.

Peptides are made in the lab using Solid Phase Peptide Synthesis (SPPS), an extremely straightforward technique that has been in use since the 1960s. Since peptides, like proteins, are PEGylated after the whole peptide has been synthesized, site-specifically PEGylating peptides requires "orthogonal protection" synthetic schemes that typically require Ph.D. level scientists to design, execute and employ more costly and dangerous reagents. The difficulty and expense has limited the ability of those of skill in the art to even study the potential for PEGylated peptides with any degree of specificity thereby hindering even the exploration of the potential impact of these materials on the market.

As discussed above, amino acids and peptides play important roles as drug compounds, in nutrition, as well as in biotechnology and other applications. Peptides, however, suffer from poor solubility, protease degradation in the body, and short shelf-lives. These problems have been very successfully solved for large proteins primarily in the pharmaceutical industry via PEGylation with large PEG polymers. The large PEG polymers, however, are too large and polydisperse for smaller peptides, thus leaving those of skill in the art without an adequate way to provide tailored PEGylated peptides for study and exploitation.

Moreover, prior art PEGylation strategies involve PEGylating amino acids, sometimes using long, polydisperse PEGs during peptide synthesis using elaborate chemical strategies that often greatly alter the original properties of the amino acids. The limited size of peptides renders these techniques unsuitable. It is difficult to control PEGylation location on the peptide and virtually impossible to form di- and tri-PEGylated amino acids in a peptide.

PEGylated lysine has been described in the past wherein the PEGylated lysine has a single PEG chain. Unfortunately, to achieve adequate functionality the PEG group length is often sufficiently long to wrap around the peptide thereby inhibiting other reactions. Furthermore, PEGylation is typically done using amide-bond-forming chemistry which inhibits the ability of the lysine to function as a salt bridge thereby mitigating a secondary function of the lysine functional group.

The present invention provides novel amino acids, novel peptides incorporating the amino acids, and a method of preparing novel peptides wherein PEGylation can be controlled, both in terms of the location on the peptide chain and in terms of the density of PEG groups, neither of which were easily controlled previously.

SUMMARY OF THE INVENTION

It is an object of the invention to provide di- and tri-PEGylated lysine and di- and tri-PEGylated glutamine.

It is an object of the invention to provide a PEGylated peptide wherein the degree of PEGylation, sites specificity of PEGylation and density of PEGylation are specifically tailored.

It is another object of the invention to provide a method for the preparation of tailored PEGylated peptides wherein the PEGylation can be incorporated systematically thereby allowing for control of the location and PEGylation density to achieve predetermined specificity.

A particular feature of the invention is the ability to form a peptide wherein selected amino acids in the peptide have multiple PEG groups thereby allowing for the use of shorter PEG groups whereby the functionality of longer PEG groups can be mimicked without the detrimental impact of PEG wrapping.

Yet another particular feature of the invention is the ability to utilize PEGylated lysine while maintaining the positively charged amine sites thereby allowing for salt bridge formation by the lysine.

These and other advantages, as will be realized, are provided in an amino acid selected from the group consisting of:

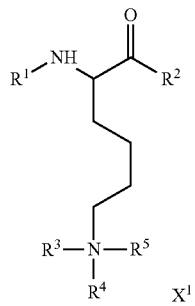

wherein:
$R^1$ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene)ethyl, 1-(4,4-dimethyl-2,6-dioxocyclohex-1-ylidene)-3-methylbutyl;
$R^2$ is selected from the group consisting of hydrogen, hydroxyl, alkyl of 1 to 5 carbons and benzyl;
$R^3$ is selected from the group consisting of hydrogen, $-(CH_2CH_2O)_mR^6$ wherein m is an integer of 0 to 25, $R^6$ is selected from the group consisting of hydrogen, alkyl of 1 to 5 carbons and $-(CH_2)_pR^7$ wherein p is an integer of 1 to 10 and $R^7$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;
$R^4$ and $R^5$ are independently selected from the group consisting of $-(CH_2CH_2O)_mR^6$ wherein m is an integer of 0 to 25, $R^6$ is selected from the group consisting of hydrogen, alkyl of 1 to 5 carbons and $-(CH_2)_pR^7$ wherein p is an integer of 1 to 10 and $R^7$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules; and
$X^1$ is a counterion to balance the charge, if necessary, wherein $X^1$ is preferably selected from the group consisting of chloride, bromide, iodide, carbonate, bicarbonate, sulfate, bisulfate, nitrate, trifluoromethansulfonate; and

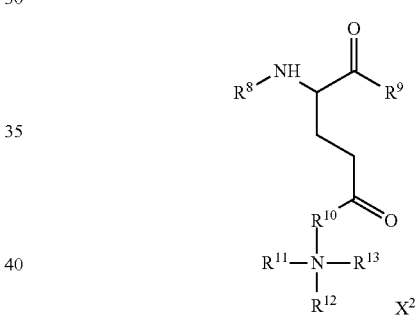

wherein:
$R^8$ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene)ethyl, 1-(4,4-dimethyl-2,6-dioxocyclohex-1-ylidene)-3-methylbutyl;
$R^9$ is selected from the group consisting of hydrogen, hydroxyl, alkyl of 1 to 5 carbons and benzyl;
$R^{10}$ represents a chemical bond or is selected from the group consisting of $N(CH_2)_q$ where q is an integer of 1 to 10 or $NCH_2CH_2(OCH_2CH_2)_r$ where r is an integer of 1 to 10;
$R^{11}$ represents a lone pair of electrons or is selected from the group consisting of a hydrogen, $-(CH_2CH_2O)_sR^{14}$ wherein s is an integer of 0 to 25 preferably 0 to 4 and more preferably 1 to 4, $R^{14}$ is selected from the group consisting of hydrogen, alkyl of 1 to 5 carbons and $-(CH_2)_tR^{15}$ wherein t is an integer of 1 to 10 and $R^{15}$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3- methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;

$R^{12}$ and $R^{13}$ are independently selected from the group consisting of —$(CH_2CH_2O)_sR^{14}$ wherein s is an integer of 0 to 25, $R^{14}$ is selected from the group consisting of hydrogen, alkyl of 1 to 5 carbons and —$(CH_2)_tR^{15}$ wherein t is an integer of 1 to 10 and $R^{15}$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules; and $X^2$ is a counterion to balance the charge, if necessary, wherein $X^2$ is preferably selected from the group consisting of chloride, bromide, iodide, carbonate, bicarbonate, sulfate, bisulfate, nitrate, trifluoromethansulfonate.

Yet another embodiment is provided in a method for forming a peptide comprising:

providing a first PEGylated amino acid selected from the group consisting of:

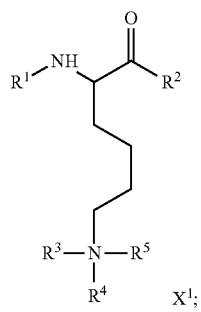

and

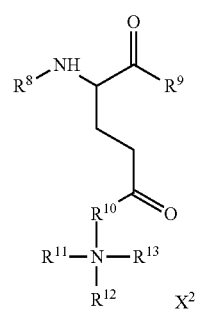

wherein the groups are defined above; and forming an amide bond between said first PEGylated amino acid of a first amino acid thereby forming said peptide.

Yet another embodiment is provided in a peptide comprising at least two amino acids wherein at least one amino acid of said amino acids is selected from the group consisting of:

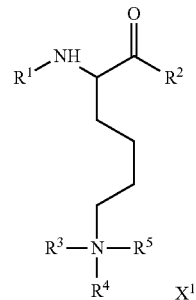

and

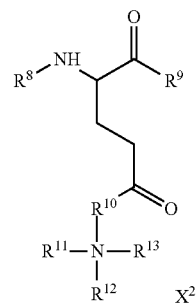

wherein the groups are as defined above.

DESCRIPTION

Figure 1:
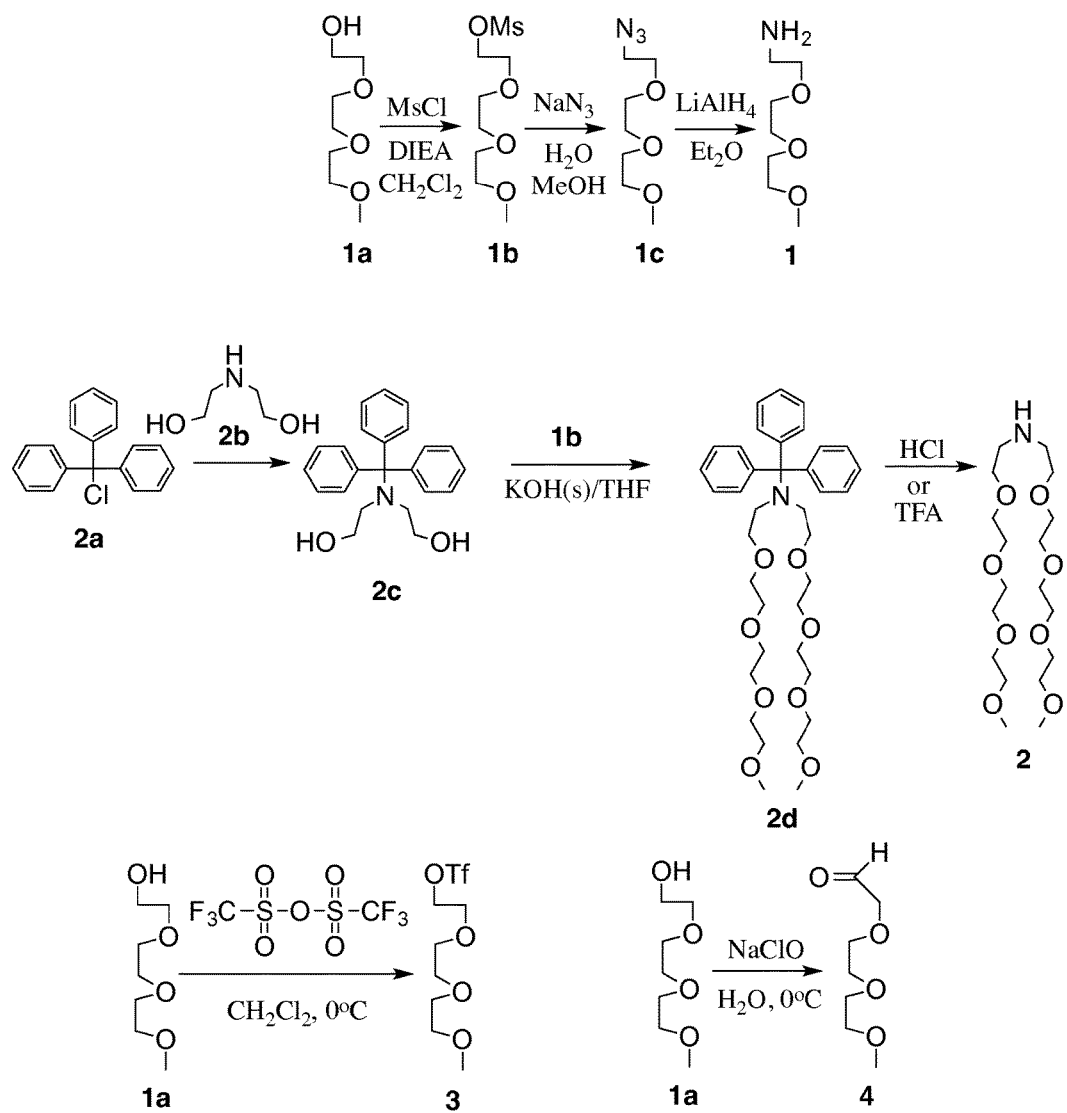
FIG. 1 schematically illustrates the synthesis of mPEG-derivatives used from tris(ethyleneglycol)monomethyl ether (TEGME).

The present invention is specific to di- and tri-PEGylated lysine and di- and tri-PEGylated glutamine and peptides formed therewith. The present invention is also specific to a method for the formation of PEGylated peptides allowing for systematic formation of PEGylated peptides wherein the location and density of PEGylation can be tailored to customize the functionality and activity of the PEGylated peptide.

The invention will be described with reference to the various figures forming an integral non-limiting component of the disclosure. Throughout the disclosure similar elements will be numbered accordingly.

The present invention is directed to PEGylated lysine derivatives and PEGylated glutamine derivatives wherein each derivative comprises at least 2 PEG units. The PEGylated lysine derivative is defined by the formula:

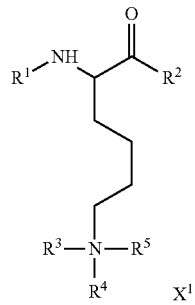

wherein:
$R^1$ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene)ethyl, 1-(4,4-dimethyl-2,6-dioxocyclohex-1-ylidene)-3-methylbutyl;
$R^2$ is selected from the group consisting of hydrogen, hydroxyl, alkyl of 1 to 5 carbons and benzyl and more preferably hydrogen, hydroxyl, methyl, ethyl, t-butyl, benzyl, succinamide, 4-nitrophenyl, and pentafluorophenyl;
$R^3$ is selected from the group consisting of hydrogen, —$(CH_2CH_2O)_mR^6$ wherein m is an integer of 0 to 25, $R^6$ is selected from the group consisting of hydrogen, alkyl of 1 to 5 carbons and —$(CH_2)_pR^7$ wherein p is an integer of 1 to 10 and $R^7$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;
$R^4$ and $R^5$ are independently selected from the group consisting of —$(CH_2CH_2O)_mR^6$ wherein m is an integer of 0 to 25, more preferably m is an integer of 0 to 4 and most preferably 1 to 4, $R^6$ is selected from the group consisting of hydrogen, alkyl of 1 to 5 carbons and —$(CH_2)_pR^7$ wherein p is an integer of 1 to 10 and $R^7$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules; and
$X^1$ is a counterion to balance the charge, if necessary, wherein $X^1$ is preferably selected from the group consisting of chloride, bromide, iodide, carbonate, bicarbonate, sulfate, bisulfate, nitrate, trifluoromethansulfonate.
In a preferred embodiment $R^3$, $R^4$ and $R^5$ are the same. In a particularly preferred embodiment $R^3$, $R^4$ and $R^5$ are —$(CH_2CH_2O)_mCH_3$ wherein m is 1 to 3.

The PEGylated glutamine derivative is defined by the formula:

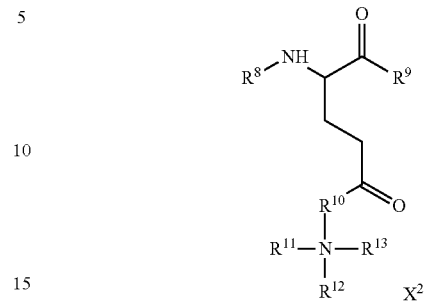

wherein:
$R^8$ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene)ethyl, 1-(4,4-dimethyl-2,6-dioxocyclohex-1-ylidene)-3-methylbutyl;
$R^9$ is selected from the group consisting of hydrogen, hydroxyl, alkyl of 1 to 5 carbons and benzyl and more preferably hydrogen, hydroxyl, methyl, ethyl, t-butyl, benzyl, succinamide, 4-nitrophenyl, and pentafluorophenyl;
$R^{10}$ represents a chemical bond or is selected from the group consisting of $N(CH_2)_q$ where q is an integer of 1 to 10 or $NCH_2CH_2(OCH_2CH_2)_r$ where r is an integer of 1 to 10;
$R^{11}$ represents a lone pair of electrons or is selected from the group consisting of a hydrogen, —$(CH_2CH_2O)_sR^{14}$ wherein s is an integer of 0 to 25 preferably 0 to 4 and more preferably 1 to 4, $R^{14}$ is selected from the group consisting of hydrogen, alkyl of 1 to 5 carbons and —$(CH_2)_tR^{15}$ wherein t is an integer of 1 to 10 and $R^{15}$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;
$R^{12}$ and $R^{13}$ are independently selected from the group consisting of —$(CH_2CH_2O)_sR^{14}$ wherein s is an integer of 0 to 25, $R^{14}$ is selected from the group consisting of hydrogen, alkyl of 1 to 5 carbons and —$(CH_2)_tR^{15}$ wherein t is an integer of 1 to 10 and $R^{15}$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules; and
$X^2$ is a counterion to balance the charge, if necessary, wherein $X^2$ is preferably selected from the group consisting of chloride, bromide, iodide, carbonate, bicarbonate, sulfate, bisulfate, nitrate, trifluoromethansulfonate.

In a preferred embodiment $R^{11}$, $R^{12}$ and $R^{13}$ are the same. In a particularly preferred embodiment $R^{11}$, $R^{12}$ and $R^{13}$ are —$(CH_2CH_2O)_mCH_3$ wherein m is 1 to 3.

For the purposes of this invention PEGylated peptides are small linear or cyclic oligomers of protein comprising at least 2 amino acids to no more than 100 amino acids wherein at least one amino acid of the PEGylated peptide is selected from the group consisting of di-PEGylated lysine, tri-PEGylated lysine, di-PEGylated glutamine and tri-PEGylated glutamine. More preferably, a peptide includes at least 5 amino acids with 10 to 100 amino acids being most preferably.

For the purposes of the present invention specific abbreviations and terms are used for brevity and clarity. Throughout the specification, "mPEG" refers to monomethoxy polyethylene glycol; "Fmoc" refers to 9-fluorenylmethyl carbamate and is typically employed in an Fmoc-protected α-amine; "Glu" refers to glutamic acid, "Gln" refer to glutamine, "Lys" refers to lysine, "MeOH" refers to methanol, "DCM" refers to dichloromethane, "THF" refers to tetrahydrofuran, "DMF" refers to N,N-dimethylformamide, "AcOH" refers to acetic acid, "TFA" refers to trifluoroacetic acid, "CDI" refers to carbonyldiimidazole, "TEGME" refers to triethyleneglycol methyl ether, "TEMPO" refers to (2,2,6,6-Tetramethylpiperidin-1-yl)oxyl, "Boc" refers to tert-butoxycarbonyl, "NEt$_3$" refers to triethylamine, "DIEA" refers to diisopropylethylamine, "Pac" refers to phenacyl, "Tfl" refers to trifluoromethanesulfonate, "Ms" refers to methanesulfonate, "Et$_2$O" refers to diethyl ether, "Boc$_2$O" refers to di-tert-butyl dicarbonate. The numerical values in the designated names refer to the number of oxygen atoms in the PEG chain. By way of example: in the term "Fmoc-Gln (mPEG-3)$_1$-OH", the "3" in mPEG-3 defines a PEG having 3 oxygen atoms therefore mPEG-3 would designate $CH_3(OCH_2CH_2)_3$—. The subscript "1" indicates the number of PEG chains attached to the amino acid, glutamine in this example. All syntheses are indicated for 3 or 4 oxygens in the PEG chain, but are the same irrespective of the PEG chain length. Lysine and Glutamine can be interchanged in the synthetic schemes illustrated herein. The terminal end is designated as either —OH or -phenacylester depicting either the presence of a free α-carboxylic acid or a phenacylester-protected α-carboxylic acid, respectively.

Formation of the PEGylated amino acid is accomplished utilizing conventional chemical techniques as augmented by the detailed description of the synthetic procedure for exemplary embodiments set forth herein. In the exemplary embodiments the length of the PEG chain is representative and one of skill in the art could alter the length without alteration of the procedure except as known in the art. In the exemplary embodiments lysine and glutamine can be used interchangeably without alteration of the procedure except as known in the art.

An embodiment of the invention will be described with reference to FIG. 1 wherein the synthesis of mPEG derivatives using tris(ethyleneglycol)monomethyl ether is illustrated schematically. In FIG. 1, an mPEG-amine, 1, was synthesized from the inexpensive commercially available tris(ethyleneglycol)monomethyl ether, 1a. Tris(ethyleneglycol)monomethyl ether (0.65 mL, 4.50 mmol) in $CH_2Cl_2$ (12 mL) was converted into a better leaving group by reacting (1.1 equiv., 0.38 mL, 4.95 mmol) methanesulfonyl chloride (MsCl) at 0° C. with (1.1 equiv., 0.86 mL, 4.95 mmol) N,N-diisopropylethylamine (DIEA) as the base. The reaction was allowed to stir for 1.5 hours before washing with brine (100 mL) and concentrating the organic phase. The residue was partitioned between hexanes and $H_2O$ in a separatory funnel. The aqueous phase was isolated and NaCl (2 g) was added before extracting the aqueous layer with $CH_2Cl_2$ (50 mL portions, 3 times). The organic layers were combined, dried over $Na_2SO_4$, and concentrated in vacuo to yield 1.08 g of 1b as a yellow oil. $^1$H NMR (CDCl$_3$, 500 MHz): δ 4.40 (t, 2H), 3.79 (t, 2H), 3.71-3.64 (m, 6H), 3.56 (t, 2H), 3.39 (s, 3H, —O—CH$_3$), 3.10 (s, 3H, —SO$_2$—CH$_3$).

With continued reference to FIG. 1, the mesylate 1b (24.2 g, 106.0 mmol) was reacted with (12 equiv., 79.0 g, 1215 mmol) sodium azide (NaN$_3$) in $H_2O$ (170 mL) and MeOH (70 mL) with slight heating for 10 hours on a sand bath to give a gentle boil open to the atmosphere. After cooling to room temperature, the aqueous phase was extracted with $CH_2Cl_2$ (150 mL portions, 4 times). The organic layers were combined, dried over $Na_2SO_4$, and concentrated in vacuo to give 1c as a yellow oil in 94.5% yield. $^1$H NMR (CDCl$_3$, 500 MHz): δ 3.71-3.67 (m, 8H), 3.57 (t, 2H), 3.42-3.39 (m, 5H).

With continued reference to FIG. 1, a reduction of the azide (1c) was done with lithium aluminum hydride in ethyl ether (Et$_2$O) or Pd-catalyzed hydrogenation to afford the desired PEG-amine, 1. The mPEG-azide (23.1 g, 132 mmol) was dissolved in dry ether (250 mL) and added dropwise over several minutes to a suspension of LiAlH$_4$ (2.19 equiv., 10.96 g, 287.2 mmol) in dry ether (150 mL) at room temperature. The reaction was allowed to stir for 1 hour under N$_2$(g) before placing the reaction in an ice-water bath. A little MeOH was slowly added first and then ice-cold $H_2O$ was added very slowly while the reaction was under N$_2$(g) until all LiAlH$_4$ reacted as judged by the end of evolution of hydrogen gas. The inorganic by-products were filtered off. Solid sodium chloride was added to reduce the solubility of mPEG-amine in water and the aqueous layer was then extracted with $CH_2Cl_2$. The organic layer was then dried over MgSO$_4$ and concentrated in vacuo to yield 1 quantitatively as a light yellow oil. $^1$H NMR (CDCl$_3$, 500 MHz): δ 3.70-3.65 (m, 6H), 3.58 (t, 2H), 3.53 (t, 2H), 3.41 (s, 3H), 2.89 (t, 2H).

With continued reference to FIG. 1, to a mixture of the commercially available diethanolamine, 2b, (1.00 g, 9.51 mmol) in $CH_2Cl_2$ (20 mL) at 0° C. was added triethylamine (1.5 equiv.), followed by the portion-wise addition of commercially available trityl chloride, 2a, (1.1 equiv). The reaction was stirred for 2 hours and then partitioned between $H_2O$ and ethyl acetate (EtOAc). The layers were separated, the organic layer washed with brine, dried over MgSO$_4$, dried in vacuo, and purified to provide the product trityl-protected diethanolamine 2c.

With continued reference to FIG. 1, to a solution of 2.1 equivalents of sodium hydride in anhydrous THF was added 1.0 equivalents of the trityl-protected diethanolamine, 2c, in THF, and allowed to react for one hour. To the mixture was added mesylated tris(ethyleneglycol) monomethyl ether (1b, 4 equiv.) and allowed to stir for an additional hour. Once finished, the organic layer was separated from the aqueous layer and washed with brine (1x), dried over MgSO$_4$, the solvent was evaporated in vacuo, and purified (if needed) to provide the product trityl-protected (mPEG-4)$_2$-amine 2d.

With continued reference to FIG. 1, the trityl-protected (mPEG-4)$_2$-amine, 2d, (3.50 g, 6.34 mmol) in 20 mL of MeOH was added dropwise at room temperature to a 20 mL solution of 5% HCl (aq). The mixture was stirred at room temperature for 15 minutes. The tritylcarbinol formed was filtered, then the solvent was evaporated under vacuum until the volume of the residue became approximately equal to the volume of the initial aqueous phase. The solution was then extracted with 15 mL of ether and the aqueous phase was basified with saturated sodium bicarbonate. Water was then evaporated, $CH_2Cl_2$ (25 mL) was added to the solid residue obtained and the mixture was stirred for 15 minutes. The remaining solid was filtered, the organic phase dried over $Na_2SO_4$, then evaporated to obtain the final product (mPEG-4)$_2$-amine 2. The product was then used without further purification.

With continued reference to FIG. 1, trifluoromethane sulfonic anhydride (1.1 equiv., 2.31 mL, 13.7 mmol) was slowly added to a solution of TEGME, 1a, (2 mL, 12.5 mmol), DIEA (4.2 equiv., 9.14 mL, 52.5 mmol), and $CH_2Cl_2$ (20 mL) to make the product (mPEG-3)$_1$-triflate 3 which was used after 2 minutes of stirring without purification in subsequent steps.

With continued reference to FIG. 1, TEGME (0.88 mL, 5.56 mmol), 1a, was dissolved in 15 mL of water with stirring at 0° C. Followed by the addition of 15 mL of commercially available bleach (5-6% Sodium hypochlorite), and 1 mol % TEMPO. The reaction was stirred for 1 hour with monitoring by TLC using hexane:ethyl acetate (8:2 v/v) as the mobile phase. Upon completion, the solvent was removed in vacuo to yield the desired product (mPEG-3)-aldehyde 4.

Figure 2:
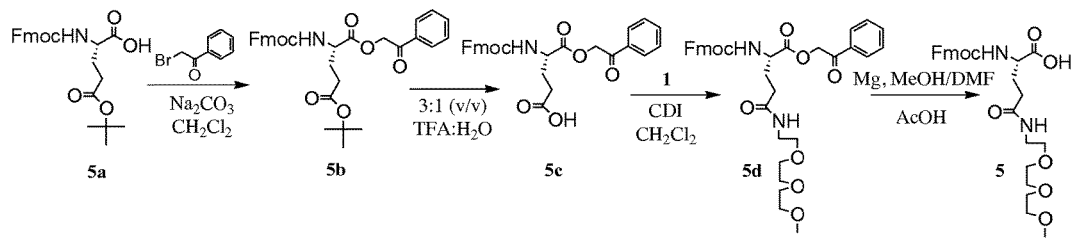
FIG. 2 schematically illustrates the synthesis of Fmoc-Gln(mPEG-3)$_1$-OH.

An embodiment of the invention will be described with reference to FIG. 2 wherein the synthesis of Fmoc-Gln (mPEG-3)$_1$-OH is illustrated schematically. With reference to FIG. 2, the synthesis of intermediates 5b and 5c were carried out by optimization of the trifluoroacetic acid (TFA): $H_2O$ ratios to ensure full cleavage of the γ-carboxylate t-butyl protection group. To an ice-cold solution of Fmoc-Glu(OtBu)-OH, 5a, (10.0 g, 23.5 mmol) in $CH_2Cl_2$ (80 mL) was added anhydrous $Na_2CO_3$ (1.1 equiv., 2.74 g, 25.9 mmol). About 2 mL of MeOH was needed to fully dissolve the Fmoc-Glu(OtBu)-OH. Phenacyl bromide (1.1 equiv., 5.15 g, 25.9 mmol) was added and the solution was allowed to slowly warm up to room temperature over 2 hours. The reaction was diluted with $CH_2Cl_2$ (50 mL) and transferred to a separatory funnel, then washed with brine (40 mL, 1×), saturated $NaCO_3$ (40 mL, 1×), and again with brine (40 mL, 1×). The organic layer was dried over $Na_2SO_4$ and dried in vacuo to give 5b in quantitative yield as an off-white (slightly yellow) solid. $[M+Na]^+$ calculated =566.6; $[M+K]^+$ calculated=582.7. $[M+Na]^+$ observed=566.8; $[M+K]^+$ observed=582.8. $^1H$ NMR (CDCl$_3$, 500 MHz): δ 7.90 (d, 2H), 7.77 (d, 2H), 7.61 (m, 3H), 7.50 (t, 2H), 7.40 (t, 2H), 7.32 (t, 2H), 5.55 (d, 1H), 5.35 (d, 1H), 4.60 (q, 1H), 4.45 (m, 2H), 4.28 (t, 1H), 2.50 (m, 2H), 2.35 (m, 1H), 2.15 (m, 1H), 1.50 (s, 9H).

With continued reference to FIG. 2, Fmoc-Glu(OtBu)-phenacylester, 5b, (6.10 g, 11.2 mmol) was dissolved in a 3:1 (v/v) TFA:$H_2O$ mixture (14 mL) at room temperature and allowed to stir for 2.5 hours. Subsequently, $CH_2Cl_2$ (20 mL) was added to the reaction while stirring. Saturated aqueous $Na_2CO_3$ was added slowly to the reaction until the acid was neutralized. The organic layer was separated, dried over $Na_2SO_4$, and dried in vacuo to yield a white solid (92.7%). The product obtained, Fmoc-Glu(OH)-phenacylester, 5c, was used in the next step without further purification. $[M+Na]^+$ calculated=510.5. $[M+Na]^+$ observed=510.8. $^1H$ NMR (DMSO-d$_6$, 500 MHz): δ 7.90 (d, 2H), 7.89 (d, 2H), 7.72 (d, 3H), 7.58 (t, 2H), 7.41 (t, 2H), 7.32 (t, 2H), 5.61 (d, 1H, —CO$_2$—CH$_2$—CO—), 5.50 (d, 1H, —CO$_2$—CH$_2$—CO—), 4.31-4.22 (m, 4H), 2.49 (t, 2H), 2.15 (m, 1H), 1.95 (m, 1H).

With continued reference to FIG. 2, the mPEG-amine, 1, was coupled with Fmoc-Glu(OH)-phenacylester, 5c, requiring some screening of the coupling reagent to ensure high yields and avoid scale-limiting chromatographic separation. The coupling was screened using four reagents to activate the carboxylic acid: diisopropylcarbodiimide (DIC), dicyclohexylcarbodiimide (DCC), 1-ethyl-3-(3-dimethylaminopropyl)carbodiimide (EDC), and carbodiimidazole (CDI). In cases of DIC, DCC, and EDC, $^1H$ NMR revealed less than optimal results, possibly due to hydrogen bonding between the urea and PEG. The use of coupling reagent CDI yielded reaction by-products $CO_2$(g) and a water soluble imidazole which, following aqueous separation, yielded a more pure product than the use of all other coupling reagents.

With continued reference to FIG. 2, carbonyldiimidazole (CDI, 1 equiv., 2.17 g, 13.4 mmol) was added to a suspension of Fmoc-Glu(OH)-phenacylester (6.53 g, 13.4 mmol) in $CH_2Cl_2$(25 mL). Activation was judged complete when effervescence subsided and everything was dissolved in solution. The solution was then poured slowly into a round-bottom flask containing mPEG-amine (1 equiv., 2 g, 13.4 mmol) and allowed to stir for 10 minutes. Another 0.5 equivalents (1.08 g, 6.7 mmol) of CDI was then added to the stirring solution and allowed to stir for 1 hour. The reaction was transferred to a separatory funnel and washed with 5% NaHCO$_3$ (1×), 0.10 M HCl (1×), and brine (1×). The organic layer was dried over $Na_2SO_4$ and concentrated under vacuum to yield 6.862 g of Fmoc-Gln(mPEG-3)$_1$-phenacylester 5d as a solid (80.9%). $[M+Na]^+$ calculated=655.7; $[M+K]^+$ calculated=671.8. $[M+Na]^+$ observed=655.7; $[M+K]^+$ observed=671.7. $^1H$ NMR (CDCl$_3$, 500 MHz): δ 7.93 (d, 2H), 7.87 (d, 2H), 7.65 (m, 3H), 7.53 (t, 2H), 7.42 (t, 2H), 7.34 (t, 2H), 5.59 (d, 1H), 5.48 (d, 1H), 4.56 (q, 1H), 4.45-4.37 (m, 2H), 4.26 (t, 1H), 3.68-3.57 (m, 11H), 3.55-3.47 (m, 4H), 3.42 (m, 5H), 2.56-2.35 (m, 3H), 2.29 (m, 1H).

With continued reference to FIG. 2, magnesium (7 equiv., 1.84 g, 75.9 mmol) and acetic acid (12 equiv., 7.44 mL, 130 mmol) were added to a solution of Fmoc-Gln(mPEG-3)$_1$-phenacylester (6.86 g, 10.8 mmol) in MeOH (25 mL) and allowed to stir for 60 minutes. $CH_2Cl_2$ was added to the reaction while stirring to dilute the reaction and magnesium was filtered out. MeOH was evaporated under $N_2$(g). The organic layer was dried over $Na_2SO_4$ and solvent was removed in vacuo before further drying on a Schlenk line to yield Fmoc-Gln(mPEG-3)$_1$-OH 5 (98.5%) as an oil. $[M+H]^+$ calculated=514.57; $[M+Na]^+$ calculated=537.56; $[M+K]^+$ calculated=553.67. $[M+H]^+$ observed=515.68; $[M+Na]^+$ observed=537.63; $[M+K]^+$ observed=553.57. $^1H$ NMR (DMSO-d$_6$, 500 MHz): δ 7.87 (d, 2H), 7.69 (d, 1H), 7.39 (t, 2H), 7.31 (t, 2H), 7.04 (s, 1H), 4.26-4.13 (m, 3H), 3.53-3.43 (m, 7H), 3.42-3.31 (m, 4H), 3.22-3.18 (m, 3H), 3.15 (m, 1H), 2.08 (t, 1H), 1.95 (m, 1H).

Another step in an embodiment of the invention is described with reference to FIG. 3 wherein the synthesis of Fmoc-Gln(mPEG-4)$_2$-OH 6 is represented schematically. The synthesis of intermediates 5b and 5c was carried out as described previously and illustrated schematically in FIG. 2. Carbonyldiimidazole (CDI, 1 equiv.) was added to a suspension of Fmoc-Glu(OH)-phenacylester 5c (1 equiv.) in $CH_2Cl_2$. Activation was completed when effervescence subsided and everything was fully dissolved. The solution was then poured slowly into a round-bottom flask containing (mPEG-4)$_2$-amine (1 equiv.), 2, and allowed to stir for 10 minutes. Another 0.5 equivalents of CDI was then added to the stirring solution and allowed to stir for 1 hour. The reaction is transferred to a separatory funnel and washed with 5% NaHCO$_3$ (1×), 0.10 M HCl (1×), and brine (1×).

The organic layer was dried over $Na_2SO_4$ and solvent was removed in vacuo to yield product Fmoc-Gln(mPEG-4)$_2$-phenacylester 6a.

Figure 3:
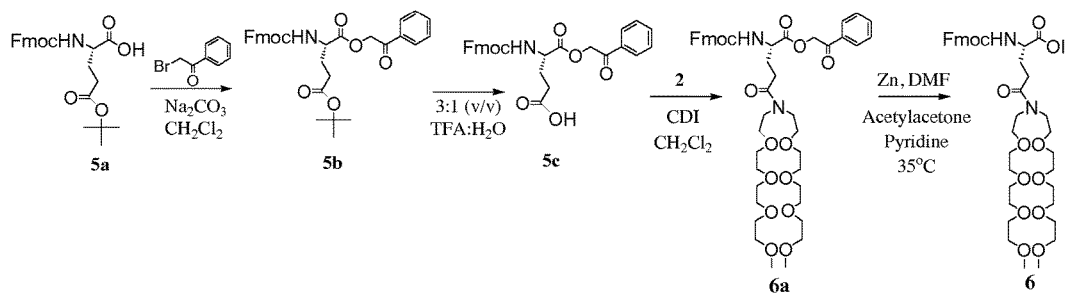
FIG. 3 schematically illustrates the synthesis of Fmoc-Gln(mPEG-4)$_2$-OH.

With continued reference to FIG. 3, to a solution of Fmoc-Gln(mPEG-4)$_2$-phenacylester (1 equiv., 5.00 g, 6.42 mmol) dissolved in DMF (20 mL) at 35° C. was added pyridine (10 mL) and acetylacetone (10 equiv.). Activated zinc dust (10 equiv.) was added and the mixture was stirred under nitrogen for 0.6 hours. To "activate" zinc dust before use, it is washed several times with 5% hydrochloric acid and washed in turn with water, methanol, and ether before drying. The reaction mixture was filtered and then dried in vacuo to yield Fmoc-Gln(mPEG-4)$_2$-OH 6.

Another step in an embodiment of the invention is described with reference to FIG. 4 wherein the synthesis of Fmoc-Lys(mPEG-3)$_3$-OH 7 is illustrated schematically. Commercially available Fmoc-Lys(Boc)-OH, 7a, was protected at the a-carboxylic acid with a phenacylester. To an ice-cold suspension of Fmoc-Lys(Boc)-OH (10.0 g, 21.3 mmol) in $CH_2Cl_2$ (20 mL) was added anhydrous $Na_2CO_3$ (1.1 equiv., 2.49 g, 23.5 mmol) and water (10 mL). A little bit of MeOH (~2 mL in this instance) was needed to fully dissolve the Fmoc-Lys(Boc)-OH. Phenacyl bromide (1.1 equiv., 4.67 g, 23.5 mmol) was added along with a small spatula tip of tetra-n-butylammonium bromide and allowed to stir for 1 hour at room temperature. The reaction was diluted with $CH_2Cl_2$ (20 mL) and transferred to a separatory funnel. The organic layer washed with brine (10 mL, 1×), saturated sodium carbonate (10 mL, 1×), and again with brine (10 mL, 1×). The organic layer was dried over $Na_2SO_4$ and dried in vacuo to yield Fmoc-Lys(Boc)-phenacylester 7b as a white solid. $[M+Na]^+$ calculated=608.7. $[M+Na]^+$ observed=609.5. $^1$H NMR (CDCl$_3$, 500 MHz): δ 7.91 (d, 2H), 7.76 (d, 2H), 7.61 (t, 3H), 7.49 (t, 2H), 7.39 (t, 2H), 7.31 (t, 2H), 5.56 (d, J=16 Hz, 1H), 5.27 (d, J=16 Hz, 2H), 4.90 (br, 1H), 4.55 (m, 1H), 4.44-4.35 (m, 2H), 4.23 (t, 1H), 3.17 (br, 2H), 2.04 (br, 1H), 1.90 (br, 1H), 1.75 (br, 1H), 1.62-1.47 (m, 4H), 1.43 (s, 9H).

Figure 4:
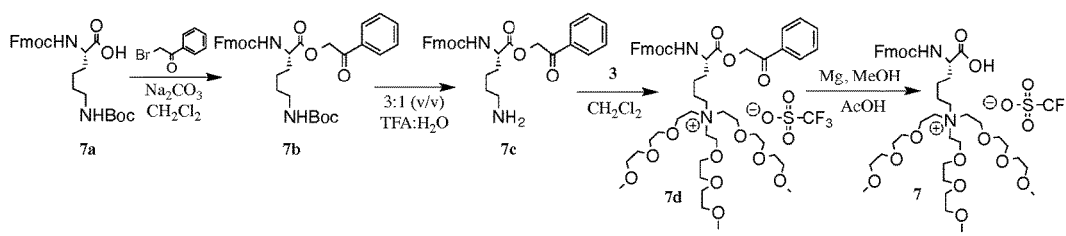
FIG. 4 schematically illustrates the synthesis of Fmoc-Lys(mPEG-3)$_3$-OH.

With continued reference to FIG. 4, Fmoc-Lys(Boc)-phenacylester (12.49 g, 21.28 mmol) was dissolved in a 3:1 (v/v) TFA:$H_2O$ (20 mL) mixture at room temperature and allowed to stir for 4 hours. $CH_2Cl_2$ was added to the reaction while stirring. Saturated $Na_2CO_3$ was added slowly to the reaction to neutralize the acid. The organic layer was separated, dried over $Na_2SO_4$, and dried in vacuo to quantitatively yield a slightly orange solid. The product Fmoc-Lys(NH$_2$)-phenacylester 7c was used in the next step without further purification.

$[M+H]^+$ calculated=487.5; $[M+Na]^+$ calculated=509.5; $[M+K]^+$ calculated=525.6. $[M+H]^+$ observed=487.6; $[M+Na]^+$ observed=509.5; $[M+K]^+$ observed=525.6. $^1$H NMR (DMSO-d$_6$, 500 MHz): δ 7.95 (d, 2H), 7.87 (d, 2H), 7.70 (m, 3H), 7.54 (t, 2H), 7.39 (t, 2H), 7.31 (t, 2H), 5.59 (d, 1H), 5.47 (d, 1H), 4.36-4.12 (m, 5H), 2.77 (m, 1H), 1.86 (m, 1H), 1.73 (m, 1H), 1.67-1.29 (m, 5H), 1.09 (s, 1H).

With continued reference to FIG. 4, mPEG-triflate, 3, was made in situ as described above. The reaction mixture containing 3 (3.3 equiv.) was transferred to a solution of Fmoc-Lys(NH$_2$)-phenacylester (2.00 g, 4.12 mmol) in $CH_2Cl_2$ (7 mL) at 0° C. and allowed to stir for 3 hours at 0° C. The crude product Fmoc-Lys(mPEG-3)$_3$-phenacylester 7d was partially purified using flash chromatography on a silica gel column with a $CH_2Cl_2$:MeOH solvent mixture in a gradient from 0% MeOH to 2% MeOH slowly to yield a golden yellow solid product (73.4%) after solvent removed. TLC of the product in 5% MeOH (in $CH_2Cl_2$) shows the product with an $R_f$ of 0.42. Some DIEA was observed in the product after the column, but the product was used in the next step without further purification. $^1$H NMR (CDCl$_3$, 500 MHz): δ 7.85 (dd, 1H), 7.82 (d, 2H), 7.68 (d, 2H), 7.58-7.53 (m, 3H), 7.45-7.40 (m, 3H), 7.31 (t, 2H), 7.24 (t, 1H), 5.46 (d, 1H), 5.23 (d, 1H), 4.46-4.28 (m, 3H), 4.15 (t, 1H), 3.84-3.80 (br, 3H), 3.78-3.68 (m, 3H), 3.66-3.64 (m, 11H), 3.61-3.56 (m, 42H), 3.55-3.51 (m, 15H), 3.50-3.47 (m, 19H), 3.30 (s, 19H), 3.24 (s, 5H), 3.15-2.94 (br, 9H), 2.02-1.93 (m, 1H), 1.90-1.82 (m, 1H), 1.77 (br, 2H), 1.46 (br, 2H), 1.31 (d, 2H), 1.24 (d, 2H).

With continued reference to FIG. 4, magnesium (7 equiv., 0.384 g, 15.79 mmol) and acetic acid (12 equiv., 1.55 mL, 27.1 mmol) were added to a solution of Fmoc-Lys(mPEG-3)$_3$-phenacylester (2.426 g, 2.25 mmol) in MeOH (20 mL) and allowed to stir for 60 minutes. $CH_2Cl_2$ was added to the reaction while stirring to dilute the reaction and magnesium was filtered out. MeOH was evaporated under $N_2$ (g). The organic layer dried over $Na_2SO_4$ and dried in vacuo before further drying on Schlenk line to quantitatively yield Fmoc-Lys(mPEG-3)$_3$-OH 7 as a white solid. $[M]^+$ calculated=807.5. $[M]^+$ observed=807.9. $^1$H NMR (CDCl$_3$, 500 MHz): δ 7.69 (d, 2H), 7.57 (d, 2H), 7.32 (t, 2H), 7.24 (t, 2H), 4.33-4.11 (m, 4H), 3.80 (br, 4H), 3.67 (t, 8H), 3.64-3.57 (m, 38H), 3.56-3.53 (t, 11H), 3.51-3.47 (t, 19H), 3.45-3.39 (m, 6H), 3.31 (s, 17H), 3.26 (s, 6H), 1.74 (br, 3H), 1.53 (s, 1H), 1.42 (s, 1H), 1.35 (d, 2H), 1.24 (d, 2H).

An embodiment of the invention is described with reference to FIG. 5 wherein the synthesis of Fmoc-Lys(N$^\varepsilon$-Boc, N$^\varepsilon$-mPEG-3)$_1$-OH 8 is illustrated schematically. The synthesis of intermediate products 7b and 7c were performed as mentioned previously for the synthesis of compound 7 as described above and illustrated schematically in FIG. 4. The synthesis of the PEG-aldehyde, 4, is performed as described above.

Figure 5:
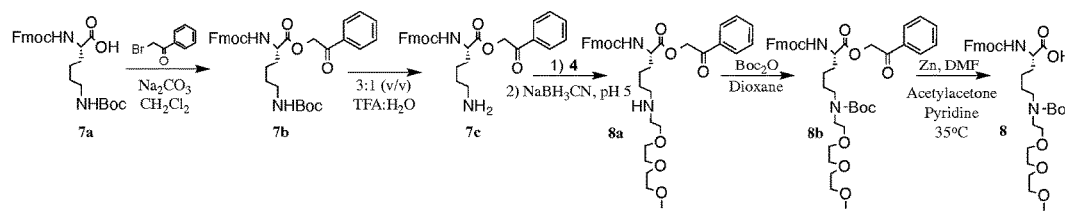
FIG. 5 schematically illustrates the synthesis of $N^\alpha$-Fmoc-Lys($N^\epsilon$-Boc, $N^\epsilon$-mPEG-3)$_1$-OH.

With continued reference to FIG. 5, a direct reductive amination was performed by mixing 7c (1 equiv.) with 4 (1 equiv.) in water (pH 5) in the presence of sodium cyanoborohydride (NaBH$_3$CN, 1 equiv.), which reduced a protonated imine to form 8a but will not reduce the aldehyde starting reagent (4).

With continued reference to FIG. 5, the addition of Boc anhydride (Boc$_2$O, 1.1 equiv.) in dioxane to the product 8a protects the N$^\varepsilon$ nitrogen. The reaction was monitored by disappearance of the amine using TLC and a ninhydrin test. Once finished, the organic layer was separated from the aqueous layer and washed with brine (1×), dried over MgSO$_4$, solvent was removed in vacuo, and purified (if needed) to provide the product Fmoc-Lys(N$^\varepsilon$-Boc, N$^\varepsilon$-mPEG-3)$_1$-phenacylester 8b.

With continued reference to FIG. 5, to a solution of Fmoc-Lys(N$^\varepsilon$-Boc, N$^\varepsilon$-mPEG-3)$_1$-phenacylester (1 equiv., 5.00 g, 4.65 mmol) dissolved in DMF (20 mL) at 35° C. was added pyridine (10 mL) and acetylacetone (10 equiv.). Then activated zinc dust (10 equiv.) was added and the mixture was stirred under nitrogen for 0.6 hours. To "activate" zinc dust before use, it is washed several times with 5% hydrochloric acid and washed in turn with water, methanol, and ether before drying. The reaction mixture was filtered and then dried in vacuo to yield Fmoc-Lys(mPEG-3)$_3$-OH 8.

An embodiment of the invention will be described with reference to FIG. 6 wherein the synthesis of Fmoc-Gln(CH$_2$CH$_2$N(mPEG-3))$_3$-OH is illustrated schematically. With reference FIG. 6, the synthesis of intermediates 5b and 5c were carried out by optimization of the trifluoroacetic acid (TFA):$H_2O$ ratios to ensure full cleavage of the γ-carboxylate t-butyl protection group. To an ice-cold solution of Fmoc-Glu(OtBu)-OH, 5a, (10.0 g, 23.5 mmol) in $CH_2Cl_2$ (80 mL) was added anhydrous $Na_2CO_3$ (1.1 equiv., 2.74 g, 25.9 mmol). About 2 mL of MeOH was needed to fully dissolve the Fmoc-Glu(OtBu)-OH. Phenacyl bromide (1.1 equiv., 5.15 g, 25.9 mmol) was added and the solution was allowed to slowly warm up to room temperature over 2 hours. The reaction was diluted with $CH_2Cl_2$ (50 mL) and transferred to a separatory funnel, then washed with brine (40 mL, 1×), saturated $NaCO_3$ (40 mL, 1×), and again with brine (40 mL, 1×). The organic layer was dried over $Na_2SO_4$ and dried in vacuo to give 5b in quantitative yield as an off-white (slightly yellow) solid. $[M+Na]^+$ calculated=566.6; $[M+K]^+$ calculated=582.7. $[M+Na]^+$ observed=566.8; $[M+K]^+$ observed=582.8. $^1H$ NMR ($CDCl_3$, 500 MHz): δ 7.90 (d, 2H), 7.77 (d, 2H), 7.61 (m, 3H), 7.50 (t, 2H), 7.40 (t, 2H), 7.32 (t, 2H), 5.55 (d, 1H), 5.35 (d, 1H), 4.60 (q, 1H), 4.45 (m, 2H), 4.28 (t, 1H), 2.50 (m, 2H), 2.35 (m, 1H), 2.15 (m, 1H), 1.50 (s, 9H).

Figure 6:
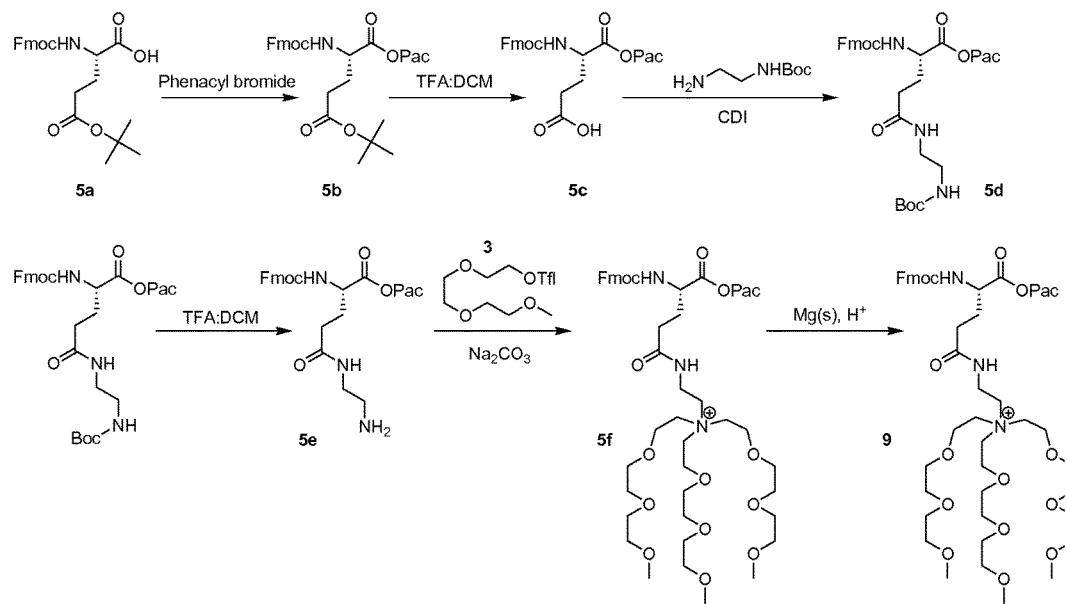
FIG. 6 schematically illustrates the synthesis of Fmoc-Gln(CH$_2$CH$_2$N(mPEG-3))$_3$-OH.

With continued reference to FIG. 6, Fmoc-Glu(OtBu)-phenacylester, 5b, (6.10 g, 11.2 mmol) was dissolved in a 3:1 (v/v) $TFA:H_2O$ mixture (14 mL) at room temperature and allowed to stir for 2.5 hours. Subsequently, $CH_2Cl_2$ (20 mL) was added to the reaction while stirring. Saturated aqueous $Na_2CO_3$ was added slowly to the reaction until the acid was neutralized. The organic layer was separated, dried over $Na_2SO_4$, and dried in vacuo to yield a white solid (92.7%). The product obtained, Fmoc-Glu(OH)-phenacylester, 5c, was used in the next step without further purification. $[M+Na]^+$ calculated=510.5. $[M+Na]^+$ observed=510.8. $^1H$ NMR (DMSO-$d_6$, 500 MHz): δ 7.90 (d, 2H), 7.89 (d, 2H), 7.72 (d, 3H), 7.58 (t, 2H), 7.41 (t, 2H), 7.32 (t, 2H), 5.61 (d, 1H, —$CO_2$—$CH_2$—CO—), 5.50 (d, 1H, —$CO_2$—$CH_2$—CO—), 4.31-4.22 (m, 4H), 2.49 (t, 2H), 2.15 (m, 1H), 1.95 (m, 1H).

With continued reference to FIG. 6, Fmoc-Glu(OH)-phenacylester, 5c, (1.0 eq) was stirred with CDI (1.1 eq) for 30 minutes in dichloromethane, followed by addition of tert-butyl N-(2-aminoethyl)carbamate (1.0 eq). The solution was stirred for an additional 3 hours during which the reaction was monitored for completion using thin layer chromatography and additional CDI was added as needed. Upon completion of the reaction it was extracted 2× with a 0.1M HCl solution, then 2× with a 0.1M $Na_2CO_3$ solution, then evaporated to dryness in vacuo, yielding Fmoc-Glu($CH_2CH_2NHBoc$)-phenacylester, 5d.

With continued reference to FIG. 6, Fmoc-Glu($CH_2CH_2NHBoc$)-phenacylester, 5d, was stirred in a 3:1 TFA:DCM solution for 3 hours at room temperature, then evaporated to dryness in vacuo, yielding Fmoc-Glu($CH_2CH_2NH_2$)-phenacylester, 5e.

With continued reference to FIG. 6, mPEG-triflate, 3, was made in situ as described above. The reaction mixture containing 3 (3.3 equiv.) was transferred to a solution of Fmoc-Glu($CH_2CH_2NH_2$)-phenacylester in dichloromethane at 0° C. and allowed to warm to room temperature for 2 hours. The reaction was then directly purified using flash silica gel column chromatography with a gradient of methanol (0-4%) in dichloromethane, yielding Fmoc-Gln($CH_2CH_2N(mPEG-3))_3$-phenacylester, 5f.

With continued reference to FIG. 6, to Fmoc-Gln($CH_2CH_2N(mPEG-3))_3$-phenacylester, 5f, (1.0 equiv.) dissolved in DMF (20 mL) at 35° C. was added pyridine (10 mL) and acetylacetone (10 equiv.). Then activated zinc dust (10 equiv.) was added and the mixture was stirred under nitrogen for 1 hour. To activate zinc dust before use, it is washed several times with 5% hydrochloric acid and washed in turn with water, methanol, and ether before drying. The reaction mixture was filtered and then dried in vacuo to yield Fmoc-Gln($CH_2CH_2N(mPEG-3))_3$-OH, 9.

The di-PEGylated lysine tri-PEGylated lysine, di-PEGylated glutamine or tri-PEGylated glutamine are particularly suitable for use in the formation of a peptide by conventional Solid Phase Peptide Synthesis (SPPS). The formation of peptides by SPPS is well known to those of skill in the art and utilization of the PEGylated amino acids described herein can be accomplished without undue experimentation. By way of example, FIGS. 7 and 8 provide general descriptions whereby multi-PEGylated lysine is incorporated into a peptide.

Figure 7:
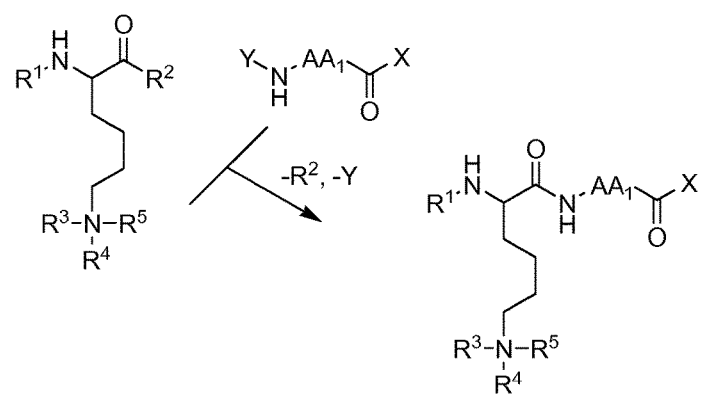
FIGS. 7 and 8 schematically illustrate the synthesis of a peptide.

With reference to FIG. 7, PEGylated lysine, which is described above, is coupled to an amino acid, designated AA1, through a peptide couple wherein the carboxyl group reacts with an amine of the amino acid to form an amide bond between the PEGylated lysine and the amino acid. As would be realized to those of skill in the art the synthetic scheme illustrated in FIG. 6 provides a simple peptide with two amino acids with one of the amino acids being the PEGylated lysine and the other represented by AA1.

Figure 8:
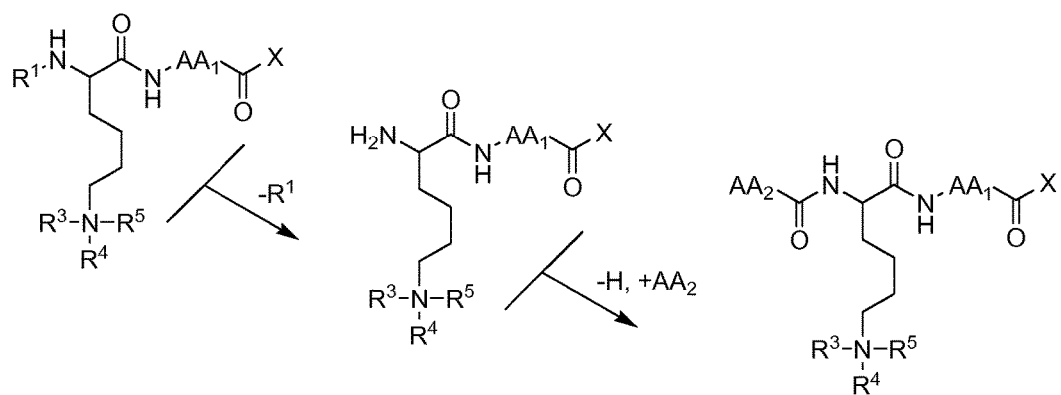

With reference to FIG. 8, the simple peptide illustrated in FIG. 7 can be further extended to include a third amino acid, designated AA2. For the purposes of illustration the protected nitrogen of the lysine is converted to an amine wherein the amine is then coupled, through peptide coupling chemistry, to a carboxylic acid group of amino acid AA2, thereby forming the amide bond between the lysine and amino acid AA2. The embodiment of FIG. 8 therefore forms a peptide with three amino acids, AA2-lysine-AA1, wherein the lysine is PEGylated. It would be readily understood to those in the art that the reaction scheme illustrated in FIGS. 7 and 8 could be extended to achieve a peptide of any desired length obtained by sequential formation of amide bonds between adjacent amino acids. It would also be understood that the peptide would include at least one derivatized amino acid selected from di-PEGylated lysine tri-PEGylated lysine, di-PEGylated glutamine or tri-PEGylated glutamine in either a terminal position or in any position within the string of amino acids within the peptide without limit to the number or position of the PEGylated amino acids.

As would be realized, the PEGylated amino acids described herein can be incorporated into a peptide wherein the peptide has, in addition to the PEGylated amino acid any combination of amino acids selected from the group consisting of: arginine, histidine, lysine, aspartic acid, glutamic acid, serine, threonine, asparagine, glutamine, cysteine, selenocystene, glycine, proline, alanine, valine, isoleucine, leucine, methionine, phenylalanine, tyrosine and tryptophan, as well as additional modified and/or unnatural amino acids.

Throughout the description references to an amino acid includes all stereoisomers of the amino acid singularly or collectively unless specifically stated otherwise.

The invention has been described with reference to the preferred embodiments without limit thereto. One of skill in the art would realize additional embodiments and improvements which are not specifically set forth herein but which are within the scope of the invention as more specifically set forth in the claims appended hereto.

The invention claimed is:
1. An amino acid selected from the group consisting of:

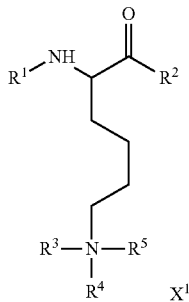

wherein:
R$^1$ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene)ethyl, and 1-(4,4-dimethyl-2,6-dioxocyclohex-1-ylidene)-3-methylbutyl;
R$^2$ is selected from the group consisting of hydrogen, hydroxyl, alkyl of 1 to 5 carbons, benzyl, succinamide, 4-nitrophenyl, and pentafluorophenyl;
R$^3$ and R$^4$ are independently selected from the group consisting of hydrogen, —(CH$_2$CH$_2$O)mR$^6$ and —(CH$_2$)$_p$R$^7$;
R$^5$ is —(CH$_2$CH$_2$O)$_m$R$^6$;
R$^6$ is selected from the group consisting of alkyl of 1 to 5 carbons and —(CH$_2$)$_p$R$^7$;
m is an integer of 1 to 25;
p is an integer of 1 to 10; and
R$^7$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;
and
X$^1$ is a counterion to balance the charge; and

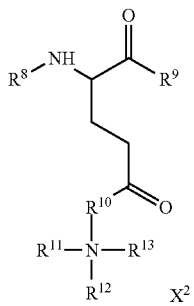

wherein:
R$^8$ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene)ethyl, and 1-(4,4-dimethyl-2,6-dioxocyclohex-1-ylidene)-3-methylbutyl;
R$^9$ is selected from the group consisting of hydrogen, hydroxyl, alkyl of 1 to 5 carbons and benzyl;
R$^{10}$ represents a chemical bond or is selected from the group consisting of —NH(CH$_2$)$_q$— where q is an integer of 1 to 10 and —NHCH$_2$CH$_2$(OCH$_2$CH$_2$)$_r$— where r is an integer of 1 to 10;
R$^{11}$ and R$^{12}$ represent a lone pair of electrons otherwise R$^{11}$ and R$^{12}$ are independently selected from the group consisting of a hydrogen, —(CH$_2$CH$_2$O)$_s$R$^{14}$ and —(CH$_2$)$_t$R$^{15}$;
R$^{13}$ is —(CH$_2$CH$_2$O)$_s$R$^{14}$;
R$^{14}$ is selected from the group consisting of alkyl of 1 to 5 carbons and —(CH$_2$)$_t$R$^{15}$;
s is an integer of 1 to 25;
t is an integer of 1 to 10; and
R$^{15}$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;
and
X$^2$ is a counterion to balance the charge if necessary.

2. The amino acid of claim 1 wherein R$^1$ is selected from the group consisting of hydrogen, t-butoxycarbonyl, fluorenylmethyloxycarbonyl and benzyloxycarbonyl.

3. The amino acid of claim 1 wherein R$^2$ is selected from the group consisting of hydrogen, hydroxyl, methyl, ethyl, t-butyl, benzyl, succinamide, 4-nitrophenyl, and pentafluorophenyl.

4. The amino acid of claim 3 wherein R$^2$ is hydroxyl.

5. The amino acid of claim 1 wherein R$^6$ is methyl.

6. The amino acid of claim 1 wherein at least two of R$^3$, R$^4$ and R$^5$ are the same.

7. The amino acid of claim 6 wherein at least two of R$^3$, R$^4$ and R$^5$ are —(CH$_2$CH$_2$O)$_m$CH$_3$ wherein m is 1 to 3.

8. The amino acid of claim 1 wherein at least two of R$^3$, R$^4$ and R$^5$ are —(CH$_2$CH$_2$O)$_m$R$^6$ wherein m is 1 to 4.

9. The amino acid of claim 8 wherein R$^6$ is —(CH$_2$)$_t$R$^7$ wherein t is an integer of 2 to 4 and R$^7$ is selected from the group consisting of allyloxycarbonylamine, t-butoxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, azide, alkyne, biotinamide and fluorescent molecules.

10. The amino acid of claim 1 wherein R$^8$ is selected from the group consisting of hydrogen, t-butoxycarbonyl, fluorenylmethyloxycarbonyl and benzyloxycarbonyl.

11. The amino acid of claim 1 wherein R$^9$ is selected from the group consisting of hydrogen, methyl, ethyl, t-butyl, and benzyl.

12. The amino acid of claim 1 wherein R$^9$ is hydroxyl.

13. The amino acid of claim 1 wherein R$^{10}$ represents a chemical bond.

14. The amino acid of claim 1 wherein R$^{10}$ is —NHCH$_2$CH$_2$—.

15. The amino acid of claim 1 wherein at least two of R$^{11}$, R$^{12}$ and R$_{13}$ are the same.

16. The amino acid of claim 15 wherein at least two of $R^{11}$, $R^{12}$ and $R^{13}$ are —$(CH_2CH_2O)_sCH_3$ wherein s is 1 to 3.

17. The amino acid of claim 1 wherein at least two of $R_{11}$, $R_{12}$ and $R^{13}$ are —$(CH_2CH_2O)_sR^{14}$ wherein s is 1 to 4.

18. The amino acid of claim 17 wherein $R^{14}$ is —$(CH_2)_t R^{15}$ wherein t is an integer of 2 to 4 and $R^{15}$ is selected from the group consisting of allyloxycarbonylamine, t-butoxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, azide, alkyne, biotinamide and fluorescent molecules.

19. A method for forming a peptide comprising:
providing a first PEGylated amino acid selected from the group consisting of:

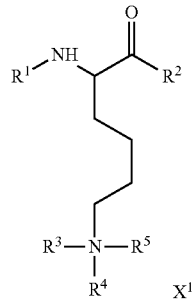

wherein:
$R^1$ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene)ethyl, and 1-(4,4-dimethyl-2,6-dioxocyclohex-1-ylidene)-3-methylbutyl;

$R^2$ is selected from the group consisting of hydrogen, hydroxyl, alkyl of 1 to 5 carbons, benzyl, succinamide, 4-nitrophenyl, and pentafluorophenyl;

$R^3$ and $R^4$ are independently selected from the group consisting of hydrogen, —$(CH_2CH_2O)_mR^6$ and —$(CH_2)_pR^7$;

$R^5$ is —$(CH_2CH_2O)_mR^6$;

$R^6$ is selected from the group consisting of alkyl of 1 to 5 carbons and —$(CH_2)_pR^7$;

m is an integer of 1 to 25;

p is an integer of 1 to 10; and $R^7$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;

and
$X^1$ is a counterion to balance the charge; and

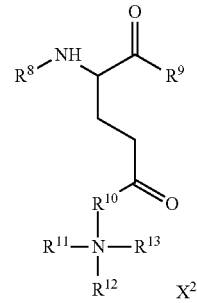

wherein:
$R^8$ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene) ethyl, and 1-(4,4-dimethyl-2,6-dioxocyclohex-1-ylidene)-3-methylbutyl;

$R^9$ is selected from the group consisting of hydrogen, hydroxyl, alkyl of 1 to 5 carbons and benzyl;

$R^{10}$ represents a chemical bond or is selected from the group consisting of —$NH(CH_2)_q$— where q is an integer of 1 to 10 and —$NHCH_2CH_2(OCH_2CH_2)_r$— where r is an integer of 1 to 10;

$R^{11}$ and $R^{12}$ represent a lone pair of electrons otherwise $R^{11}$ and $R^{12}$ are independently selected from the group consisting of a hydrogen, —$(CH_2CH_2O)_sR^{14}$ and —$(CH_2)_tR^{15}$;

$R^{13}$ is —$(CH_2CH_2O)_sR^{14}$;

$R^{14}$ is selected from the group consisting of alkyl of 1 to 5 carbons and —$(CH_2)_tR^{15}$;

s is an integer of 1 to 25;

t is an integer of 1 to 10; and $R^{15}$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;

and
$X^2$ is a counterion to balance the charge if necessary; and forming an amide bond between said first PEGylated amino acid and a first amino acid thereby forming said peptide.

20. The method for forming a peptide of claim 19 wherein $R^1$ is selected from the group consisting of hydrogen, t-butoxycarbonyl, fluorenylmethyloxycarbonyl and benzyloxycarbonyl.

21. The method for forming a peptide of claim 19 wherein $R^2$ is selected from the group consisting of hydrogen, hydroxyl, methyl, ethyl, t-butyl, benzyl, succinamide, 4-nitrophenyl, and pentafluorophenyl.

22. The method for forming a peptide of claim 21 wherein $R^2$ is hydroxyl.

23. The method for forming a peptide of claim 19 wherein $R^6$ is methyl.

24. The method for forming a peptide of claim 19 wherein at least two of R³, R⁴ and R⁵ are the same.

25. The method for forming a peptide of claim 24 wherein at least two of R³, R⁴ and R⁵ are —(CH₂CH₂O)$_m$CH₃ wherein m is 1 to 3.

26. The method for forming a peptide of claim 19 wherein at least two of R³, R⁴ and R⁵ are —(CH₂CH₂O)$_m$R⁶ wherein m is 1 to 4.

27. The method for forming a peptide of claim 26 wherein R⁶ is —(CH₂)$_t$R⁷ wherein t is an integer of 2 to 4 and R⁷ is selected from the group consisting of allyloxycarbonylamine, t-butoxycarbonylamine, tritylamine, 4-methyltritylamine, 4-methoxytritylamine, 1-(4,4-dimethyl-2,6-dioxocyclohex-1-ylidene) ethylamine, 1-(4,4-dimethyl-2,6-dioxocyclohex-1-ylidene)-3-methylbutylamine, azide, alkyne, biotinamide and fluorescent molecules.

28. The method for forming a peptide of claim 19 wherein R⁸ is selected from the group consisting of hydrogen, t-butoxycarbonyl, fluorenylmethyloxycarbonyl and benzyloxycarbonyl.

29. The method for forming a peptide of claim 19 wherein R⁹ is selected from the group consisting of hydrogen, methyl, ethyl, t-butyl, and benzyl.

30. The method for forming a peptide of claim 19 wherein R⁹ is hydroxyl.

31. The method for forming a peptide of claim 19 wherein R¹⁰ represents a chemical bond.

32. The method for forming a peptide of claim 19 wherein R¹⁰ is —NHCH₂CH₂—.

33. The method for forming a peptide of claim 19 wherein at least two of R¹¹, R¹² and R¹³ are the same.

34. The method for forming a peptide of claim 33 wherein at least two of R¹¹, R¹² and R¹³ are —(CH₂CH₂O)$_s$CH₃ wherein s is 1 to 3.

35. The method for forming a peptide of claim 19 wherein at least two of R¹¹, R¹² and R¹³ are —(CH₂CH₂O)$_s$R¹⁴ wherein s is 1 to 4.

36. The method for forming a peptide of claim 35 wherein R¹⁴ is —(CH₂)$_t$R¹⁵ wherein t is an integer of 2 to 4 and R¹⁵ is selected from the group consisting of allyloxycarbonylamine, t-butoxycarbonylamine, tritylamine, 4-methyltritylamine, 4-methoxytritylamine, 1-(4,4-dimethyl-2,6-dioxocyclohex-1-ylidene) ethylamine, 1-(4,4-dimethyl-2,6-dioxocyclohex-1-ylidene) -3-methylbutylamine, azide, alkyne, biotinamide and fluorescent molecules.

37. The method for forming a peptide of claim 19 further comprising forming a second amide bond between a second amino acid and one of said first amino acid and said first PEGylated amino acid thereby extending said peptide to three amino acids.

38. The method for forming a peptide of claim 37 further comprising forming at least one additional amide bond between at least one additional amino acid and said peptide.

39. The method for forming a peptide of claim 19 wherein said peptide comprises at least one of said first PEGylated amino acid and at least one amino acid selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan.

40. The method for forming a peptide of claim 19 wherein said peptide comprises at least 10 amino acids.

41. A peptide comprising at least two amino acids wherein at least one amino acid of said amino acids is a residue of an amino acid selected from the group consisting of:

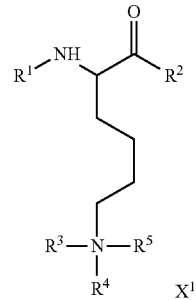

wherein:
R¹ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene) thyl, and 1-(4,4-dimethyl-2,6-dioxocyclohex-1-ylidene)-3-methylbutyl;

R² is selected from the group consisting of hydrogen, hydroxyl, alkyl of 1 to 5 carbons, benzyl, succinamide, 4-nitrophenyl, and pentafluorophenyl;

R³ and R⁴ are independently selected from the group consisting of hydrogen, —(CH₂CH₂O)mR⁶ and —(CH₂)$_p$R⁷;

R⁵ is —(CH₂CH₂O)mR⁶;

R⁶ is selected from the group consisting of alkyl of 1 to 5 carbons and —(CH₂)$_p$R⁷;

m is an integer of 1 to 25;

p is an integer of 1 to 10; and

R⁷ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4, 4-dimethyl-2,6-dioxocyclohex-1-ylidene) ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;

and

X¹ is a counterion to balance the charge; and

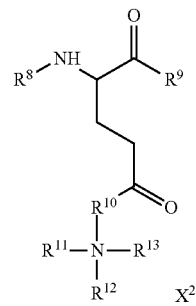

wherein:
R⁸ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene) ethyl, and 1-(4,4-dimethyl-2,6-dioxocyclohex-1-ylidene)-3-methylbutyl;

R⁹ is selected from the group consisting of hydrogen, hydroxyl, alkyl of 1 to 5 carbons and benzyl;

R¹⁰ represents a chemical bond or is selected from the group consisting of —NH(CH₂)_q— where q is an integer of 1 to 10 and —NHCH₂CH₂(OCH₂CH₂)_r— where r is an integer of 1 to 10;

R¹¹ and R¹² represent a lone pair of electrons or otherwise R¹¹ and R¹² are independently selected from the group consisting of a hydrogen, —(CH₂CH₂O)_sR¹⁴ and —(CH₂)_tR¹⁵;

R¹³ is —(CH₂CH₂O)_sR¹⁴;

R¹⁴ is selected from the group consisting of alkyl of 1 to 5 carbons and —(CH₂)_tR¹⁵;

s is an integer of 1 to 25;

t is an integer of 1 to 10; and

R¹⁵ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene) ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;

and

X² is a counterion to balance the charge, if necessary.

42. The peptide of claim 41 wherein R¹ is selected from the group consisting of hydrogen, t-butoxycarbonyl, fluorenylmethyloxycarbonyl and benzyloxycarbonyl.

43. The peptide of claim 41 wherein R² is selected from the group consisting of hydrogen, hydroxyl, methyl, ethyl, t-butyl, benzyl, succinamide, 4-nitrophenyl, and pentafluorophenyl.

44. The peptide of claim 43 wherein R² is hydroxyl.

45. The peptide of claim 41 wherein R⁶ is methyl.

46. The peptide of claim 41 wherein at least two of R³, R⁴ and R⁵ are the same.

47. The peptide of claim 46 wherein at least two of R³, R⁴ and R⁵ are —(CH₂CH₂O)_mCH₃ wherein m is 1 to 3.

48. The peptide of claim 41 wherein at least two of R³, R⁴ and R⁵ are —(CH₂CH₂O)_mR⁶ wherein m is 1 to 4.

49. The peptide of claim 48 wherein R⁶ is —(CH₂)_tR⁷ wherein t is an integer of 2 to 4 and R⁷ is selected from the group consisting of allyloxycarbonylamine, t-butoxycarbonylamine, tritylamine, 4-methyltritylamine, 4-methoxytritylamine, 1-(4,4-dimethyl-2,6-dioxocyclohex-1-ylidene) ethylamine, 1-(4,4-dimethyl-2,6-dioxocyclohex-1-ylidene)-3-methylbutylamine, azide, alkyne, biotinamide and fluorescent molecules.

50. The peptide of claim 41 wherein R⁸ is selected from the group consisting of t-butoxycarbonyl, fluorenylmethyloxycarbonyl and benzyloxycarbonyl.

51. The peptide of claim 41 wherein R⁹ is selected from the group consisting of hydrogen, hydroxyl, methyl, ethyl, t-butyl, and benzyl.

52. The peptide of claim 51 wherein R⁹ is hydroxyl.

53. The peptide of claim 41 wherein R¹⁰ represents a chemical bond.

54. The peptide of claim 41 wherein R¹⁰ is —NHCH₂CH₂—.

55. The peptide of claim 41 wherein at least two of R¹¹, R¹² and R¹³, are the same.

56. The peptide of claim 55 wherein at least two of R¹¹, R¹² and R¹³ are —(CH₂CH₂O)_sCH₃ wherein s is 1 to 3.

57. The peptide of claim 41 wherein at least two of R¹¹, R¹² and R¹³ are —(CH₂CH₂O)_sR¹⁴ wherein s is 1 to 4.

58. The peptide of claim 57 wherein R¹⁴ is —(CH₂)_tR¹⁵ wherein t is an integer of 2 to 4 and R¹⁵ is selected from the group consisting of allyloxycarbonylamine, t-butoxycarbonylamine, tritylamine, 4-methyltritylamine, 4-methoxytritylamine, 1-(4,4-dimethyl-2,6-dioxocyclohex-1-ylidene) ethylamine, 1-(4,4-dimethyl-2,6-dioxocyclohex-1-ylidene)-3-methylbutylamine, azide, alkyne, biotinamide and fluorescent molecules.

59. The peptide of claim 41 wherein said peptide comprises at least one of the PEGylated amino acids and at least one amino acid selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan.

60. The peptide of claim 41 wherein said peptide comprises at least 10 amino acids.

61. The amino acid of claim 1 wherein R⁶ is an alkyl of 3-5 carbons.

62. The method for forming a peptide of claim 19 wherein R⁶ is an alkyl of 3-5 carbons.

63. The peptide of claim 41 wherein R⁶ is an alkyl of 3-5 carbons.

64. An amino acid selected from the group consisting of:

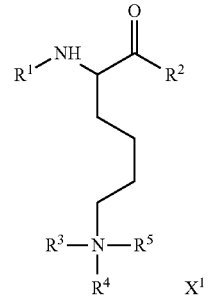

wherein:

R¹ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene)ethyl, and 1-(4,4-dimethyl-2,6-dioxocyclohex-1-ylidene)-3-methylbutyl;

R² is selected from the group consisting of hydrogen, hydroxyl, alkyl of 1 to 5 carbons, benzyl, succinamide, 4-nitrophenyl, and pentafluorophenyl;

R³ and R⁴ are independently selected from the group consisting of hydrogen, —(CH₂CH₂O)_mR⁶ and —(CH₂)_pR⁷;

R⁵ is —(CH₂CH₂O)_mR⁶;

R⁶ is selected from the group consisting of alkyl of 3 to 5 carbons and —(CH₂)_pR⁷;

m is an integer of 0 to 25;

p is an integer of 3 to 10; and

R⁷ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;
and
$X^1$ is a counterion to balance the charge; and

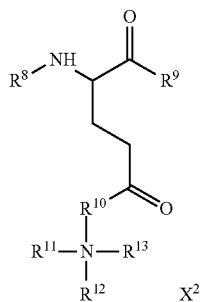

wherein:
$R^8$ is selected from the group consisting of hydrogen, allyloxycarbonyl, t-butoxycarbonyl, benzyloxycarbonyl, fluorenylmethyloxycarbonyl, trityl, 4-methyltrityl, 4-methoxytrityl, 1-(4,4-dimethyl-2,6-dioxocyclohex-1-ylidene)ethyl, and 1-(4,4-dimethyl-2,6-dioxocyclohex-1-ylidene)-3-methylbutyl;
$R^9$ is selected from the group consisting of hydrogen, hydroxyl, alkyl of 1 to 5 carbons and benzyl;
$R^{10}$ represents a chemical bond or is selected from the group consisting of $-NH(CH_2)_q-$ where q is an integer of 1 to 10 and $-NHCH_2CH_2(CH_2CH_2)_r-$ where r is an integer of 1 to 10;
$R^{11}$ and $R^{12}$ represent a lone pair of electrons otherwise $R^{11}$ and $R^{12}$ are independently selected from the group consisting of a hydrogen, $-(CH_2CH_2O)_sR^{14}$ and $-(CH_2)_tR^{15}$;
$R^{13}$ is $-(CH_2CH_2O)_sR^{14}$;
$R^{14}$ is selected from the group consisting of alkyl of 3 to 5 carbons and $-(CH_2)_tR^{15}$;
s is an integer of 1 to 25;
t is an integer of 3 to 10; and
$R^{15}$ is selected from the group consisting of allyloxycarbonylamine, t-butoxycarbonylamine, benzyloxycarbonylamine, fluorenylmethyloxycarbonylamine, tritylamine, 4-methyltritylamine, 4-methoxytritylamine, 1-(4,4-dimethyl-2,6-dioxocyclohex-1-ylidene)ethylamine, 1-(4,4-dimethyl-2,6-dioxocyclohex-1-ylidene)-3-methylbutylamine, hydroxyl, methoxy, tert-butoxy, benzyloxy, trityloxy, cholesteroloxy, acetate, carboxylic acid, methyl ester, tert-butyl ester, benzyl ester, azide, alkyne, biotin, biotinamide, cholesterol and fluorescent molecules;
and
$X^2$ is a counterion to balance the charge if necessary.

* * * * *